(12) United States Patent
Benoit et al.

(10) Patent No.: US 6,258,596 B1
(45) Date of Patent: Jul. 10, 2001

(54) VARIANTS OF APOLIPOPROTEIN A-I

(75) Inventors: Patrick Benoit, Paris; Eric Bruckert, Meudon; Patrice Denefle, Saint Maur; Nicolas Duverger, Paris; Jean-Charles Fruchart, Lambersart; Gérald Luc, Marcq en Baroeuil; Gérard Turpin, Paris, all of (FR); Gerd Assmann; Harald Funke, both of Munster (DE)

(73) Assignee: Aventis Pharmaceuticals Products Inc., Bridgewater, NJ (US)

( * ) Notice: Subject to any disclaimer, the term of this patent is extended or adjusted under 35 U.S.C. 154(b) by 0 days.

(21) Appl. No.: 08/952,796

(22) PCT Filed: Dec. 20, 1996

(86) PCT No.: PCT/US96/20739
   § 371 Date: Jun. 5, 1998
   § 102(e) Date: Jun. 5, 1998

(87) PCT Pub. No.: WO96/37608
   PCT Pub. Date: Nov. 28, 1996

(30) Foreign Application Priority Data

May 22, 1995 (FR) .................................................. 95 06061

(51) Int. Cl.[7] .......................... C07K 16/00; C12N 15/00; C12N 15/88
(52) U.S. Cl. ...................... 435/325; 435/320.1; 530/350; 536/23.1; 536/23.5
(58) Field of Search ................................. 536/23.1, 23.5; 435/69.1, 320.1, 325, 455, 458; 424/93.21; 514/2; 530/350

(56) References Cited

FOREIGN PATENT DOCUMENTS

WO 93/12143  6/1993  (WO).
WO 94/25073  11/1994  (WO).

OTHER PUBLICATIONS

Ngo et al., in The Protein Folding Problem and Tertiary Structure Prediction, 1994, Merz et al., (ed.), Birkauser, Boston, MA, pp. 492–495.*

Anderson, Nature, vol. 392, 25–30, Apr. 1998.*

Gunzburg et al., vol. 1, No. 9, pp. 410–417, 1995.*

Herzyk et al., The secondary structure of apolipoproteins in human HDL3 particles after chemical modification of their tyrosine, lysine, cysteine or arginine residues., Biochimica et Biophysica Acta 962, 131–142 (1988).

Database Swissport & J. Mol. Biol. 184, 353–366 (1988).

* cited by examiner

*Primary Examiner*—John L. LeGuyader
*Assistant Examiner*—Dave Trong Nguyen
(74) *Attorney, Agent, or Firm*—F. Aaron Dubberley; Karen I. Krupen

(57) ABSTRACT

The present invention relates to variants of the human apolipoproteine A-I comprising a cystein in position 151, the corresponding nucleic acids and the vectors containing them. It also relates to pharmaceutical compositions comprising said elements and their utilization, particularly in genic therapy.

23 Claims, 8 Drawing Sheets

VARIANTS OF APOLIPOPROTEIN A-I

This application is the U.S. National phase of International Application No. PCT/FR96/00747, filed May 20, 1996, which claimed priority to French Application No. FR/95/06061 filed May 22, 1995.

The present invention relates to a new variant of apolipoprotein A-I. It also relates to any nucleic acid coding for this new variant. It relates, in addition, to the use of this protein or these nucleic acids for therapeutic purposes. More especially, the invention relates to a new variant of apolipoprotein A-I containing, in particular, a mutation at position 151.

Apolipoprotein A-I (apoA-I) is the major constituent of the high density lipoproteins (HDL), which are macromolecular complexes composed of cholesterol, phospholipids and triglycerides. ApoA-I is a protein consisting of 243 amino acids, synthesized in the form of a preproprotein of 267 residues, having a molecular mass of 28,000 daltons. The prepro form of apoA-I is synthesized in man by both the liver and the intestine. This form of protein is then cleaved to a proprotein which is secreted into the plasma. In the vascular compartment, proapoA-I is then converted to the mature protein (243 amino acids) by the action of a calcium-dependent protease. ApoA-I has a structural role and an active role in lipoprotein metabolism: apoA-I is, in particular, a cofactor of lecithin:cholesterol acyltransferase (LCAT), responsible for the esterification of plasma cholesterol.

The level of cholesterol contained in the HDL fraction and the plasma concentration of apoA-I are negative risk factors for the development of atherosclerosis in man. Epidemiological studies have, in effect, demonstrated an inverse correlation between the concentrations of HDL cholesterol and apoA-I and the incidence of cardiovascular diseases (E. G. Miller et al., Lancet, 1977:965–968). In contrast, a longevity would appear to be associated with a high level of HDL cholesterol. Recently, the protective role of apoA-I has been demonstrated in a model of transgenic mice expressing human apolipoprotein A-I (Rubin et al., Nature). Similarly, the infusion of HDL in rabbits induces a regression of the lesions (Badimon et al., J. Clin. Invest. 85, 1234–41, 1990). Different mechanisms have been proposed to explain the protective effect of HDL, and in particular a role of HDL in the reverse transport of cholesterol (Fruchart et al., Circulation, 87: 22–27, 1993) and an antiioxidant action of HDL (Forte T., Current Opinion in Lipidology, 5: 354–364, 1994)).

The gene coding for apoA-I has been cloned and sequenced (Sharpe et al., Nucleic Acids Res. 12(9) (1984) 3917). This gene, 1863 bp in length, comprises 4 exons and 3 introns. The cDNA coding for apoA-I has also been described (Law et al., PNAS 81 (1984) 66). This cDNA comprises 840 bp (see SEQ ID No. 1). Besides the wild-type form of apoA-I, different natural variants have been described in the prior art, the differences between these variants and the wild-type protein being given in the table below:

| Variant: | Mutation | Variant | Mutation |
|---|---|---|---|
| Milano | Arg173Cys | Norway | Glu136Lys |
| Marburg | Lys107Ø | | Pro165Arg |
| Munster2B | Ala158Glu | | Pro3His |
| Giessen | Pro143Arg | | Arg10Leu |
| Munster3A | Asp103Asn | | Gly26Arg |
| Munster3B | Pro4Arg | | Asp89Glu |
| Munster3C | Pro3Arg | | Lys107Met |
| Munster3D | Asp213Gly | | Glu139Gly |
| Munster4 | Glu198Lys | | Glu147Val |
| Yame | Asp13Tyr | | Ala158Glu |
| | Asp213Gly | | Glu169Gln |
| | | | Arg177His |

The present invention is the outcome of the demonstration of a new series of variants of apolipoprotein A-I. This series of variant possesses, in particular, a replacement of the arginine residue at position 151 by a cysteine residue. The apoA-I variant according to the invention displays noteworthy therapeutic properties. In particular, it possesses especially important properties of anti-atherogenic protection. Thus, in a situation of extremely low levels of cholesterol in the HDL fraction, associated with a hypertriglyceridaemia, the presence of this variant prevents the development of any atherosclerosis, testifying to a very potent protective role, specific to this mutated apoA-I. In addition, the presence of a cysteine in the apoA-I according to the invention gives rise to the formation of dimers and other complexes linked via a disulphide bridge. This apoA-I occurs in free form in the plasma, bound as a diner to itself or combined with apolipoprotein A-II, which is another important protein associated with HDL and which also possesses a cysteine in its sequence. Moreover, the loss of the charge associated with the arginine at position 151 gives rise to the visualization of this mutant by isoelectric focusing of the plasma proteins followed by an immunological disclosure of the apoA-I.

In view of its especially noteworthy anti-atherogenic properties, this new protein according to the invention affords a substantial therapeutic advantage in the treatment and prevention of cardiovascular pathologies.

A first subject of the invention hence relates to a series of variants of human apolipoprotein A-I comprising a cysteine at position 151. The amino acid sequence of the reference apoA-I is described in the literature (see Law, cited above). This sequence, including the prepro region (residues 1 to 24), is presented in the sequence SEQ ID No. 2. A feature of the variants according to the invention hence lies in the presence of a cysteine at position 151 of th e mature apoA-I (corresponding to position 175 in the sequence SEQ ID No. 2), replacing the arginine present in the reference sequence. A preferred variant according to the invention comprises the peptide sequence SEQ ID No. 13, and still more preferably the peptide sequence lying between residues 68 and 267 of the sequence SEQ ID No. 2, residue 175 being replaced by a cysteine.

The variants according to the invention are represented, in particular, by apoA-I Paris, that is to say an apoA-I possessing a cysteine at position 151 relative to the native apoA-I. The variants according to the invention may also carry other structural modifications relative to the reference apolipoprotein A-I, and in particular other mutations, deletions and/or additions. According to a particular embodiment, the variants of the invention also comprise other mutations leading to the replacement of residues by cysteines. Thus, another particular variant combines the mutation present in the variant apoA-I Paris and apoA-I milano. Other mutations may also be present, affecting residues which do not significantly modify the properties of apoA-I. The activity of these variants may be verified, in particular, by a cholesterol efflux test.

The variants according to the invention may be obtained in different ways. They may, in the first place, be synthesized chemically by means of the techniques known to a person skilled in the art using peptide synthesizers. They may also be obtained from the reference apoA-I, by mutation(s). Advantageously, the proteins in question are recombinant, that is to say obtained by expression of a corresponding nucleic acid in a cell host, as described later.

As mentioned above, the variants according to the invention may be in monomeric form or in dimer form. The presence of at least one cysteine in the sequence of the variants of the invention makes it possible, in effect, for dimers to be produced by disulphide bonding. The dimers can be homodimers, that is to say dimers comprising two variants according to the invention (for example diApoA-I Paris); or heterodimers, that is to say dimers comprising a variant according to the invention and another molecule possessing a free cysteine (for example ApoA-I Paris:ApoA-II).

Another subject of the invention lies in a nucleic acid coding for an apolipoprotein A-I variant as defined above. The nucleic acid of the present invention can be a deoxyribonucleic acid (DNA) or a ribonucleic acid (RNA). Among DNAs, a complementary DNA (cDNA), a genomic DNA (gDNA), a hybrid sequence or a synthetic or semi-synthetic sequence may be used. The nucleic acid may, in addition, be one which is chemically modified, for example for the purpose of increasing its resistance to nucleases, its cell penetration or cell targeting, its therapeutic efficacy, and the like. These nucleic acids may be of human, animal, vegetable, bacterial, viral, synthetic, and the like, origin. They may be obtained by any technique known to a person skilled in the art, and in particular by the screening of libraries, by chemical synthesis or alternatively by mixed methods including chemical or enzymatic modification of sequences obtained by the screening of libraries.

Advantageously, the nucleic acid is a cDNA or a gDNA.

Preferably, the nucleic acid according to the invention comprises the sequence SEQ ID No 12. Still more preferably, it comprises the sequence SEQ ID No. 14.

The nucleic acid according to the invention advantageously comprises a transcription promoter region which is functional in the target cell or organism, as well as a region located at the 3' end and which specifies a transcription termination signal and a polyadenylation site. This set of elements constitutes the expression cassette. As regards the promoter region, this may be the promoter region naturally responsible for the expression of the gene for apoA-I or from a variant of ApoA-I when the latter is capable of functioning in the cell or organism concerned. The promoter region may also comprise regions of different origin (responsible for the expression of other proteins, or even synthetic regions). In particular, it may comprise promoter sequences of eukaryotic or viral genes. For example, it may comprise promoter sequences originating from the genome of the target cell. Among eukaryotic promoters, it is possible to use any promoter or derived sequence that stimulates or represses the transcription of a gene, specifically or otherwise, inducibly or otherwise, strongly or weakly. It is possible to use, in particular, ubiquitous promoters (promoter of the HPRT, PGK, vimentin, α-actin, tubulin, and the like, genes), promoters of therapeutic genes (for example the promoter of MDR, CFTR, factor VIII, and the like, genes), tissue-specific promoters (promoter of the pyruvate kinase, villin, intestinal fatty acid binding protein, smooth muscle α-actin, and the like, gene) or alternatively promoters that respond to a stimulus (steroid hormone receptor, retinoic acid receptor, and the like). Similarly, promoter sequences originating from the genome of a virus may be used, such as, for example, the promoters of the adenovirus E1A and MLP genes, the CMV early promoter, the RSV LTR promoter, and the like. In addition, these promoter regions may be modified by adding activating or regulatory sequences, or sequences permitting a tissue-specific or preponderant expression.

Moreover, the nucleic acid may also contain a signal sequence directing the synthesized product into the pathways of secretion of the target cell. This signal sequence can be the natural signal sequence of apoA-I, but it can also be any other functional signal sequence or an artificial signal sequence.

The nucleic acid according to the invention may be used to produce the recombinant ApoA-I variants by expression in a recombinant host cell, or directly as a medicinal product in applications of gene or cell therapy.

For the production of recombinant variants according to the invention, the nucleic acid is advantageously incorporated in a viral or plasmid vector, which can be an autonomously replicating or integrative vector. This vector is then used to transfect or infect a chosen cell population. The transfected or infected cells thereby obtained are then cultured under conditions permitting the expression of the nucleic acid, and the recombinant apoA-I variant according to the invention is isolated. The cell hosts which can be used for the production of the variants of the invention by recombinant means are either eukaryotic or prokaryotic hosts. Among suitable eukaryotic hosts, animal cells, yeasts or fungi may be mentioned. In particular, as regards yeasts, yeasts of the genus Saccharomyces, Kluyveromyces, Pichia, Schwanniomyces or Hansenula may be mentioned. As regards animal cells, COS, CHO, CI27, NIH-3T3, and the like, cells, may be mentioned. Among fungi, Aspergillus ssp. or Trichoderma ssp. may be mentioned more especially. As prokaryotic hosts, it is preferable to use the following bacteria: *E. coli,* Bacillus or Streptomyces. The variant thus isolated may then be packaged with a view to its therapeutic use.

According to an especially advantageous embodiment, the nucleic acid according to the invention is used directly as a medicinal product in gene or cell therapy applications. In this connection, it may be used as it is, by injection at the site to be treated or incubation with cells with a view to their administration. It has, in effect, been reported that naked nucleic acids could enter cells without a special vector. Nevertheless, it is preferable in the context of the present invention to use an administration vector, enabling (i) the efficacy of cell penetration, (ii) targeting and (iii) extra- and intracellular stability to be improved.

According to a particular embodiment, the present invention hence relates to a vector comprising a nucleic acid as defined above.

Different types of vector may be used. The vectors may be viral or non-viral.

In a preferred embodiment, the vector of the invention is a viral vector.

The use of viral vectors is based on the natural transfection properties of viruses. It is thus possible to use adenoviruses, herpesviruses, retroviruses, adeno-associated viruses or alternatively the vaccinia virus. These vectors prove especially efficacious from the standpoint of transfection.

As regards adenoviruses more especially, different serotypes whose structure and properties vary somewhat have been characterized. Among these serotypes, it is preferable to use, in the context of the present invention, human adenoviruses type 2 or 5 (Ad 2 or Ad 5) or adenoviruses of animal origin (see Application WO94/26914). Among adenoviruses of animal origin which can be used in the context of the present invention, adenoviruses of canine, bovine, murine (for example Mav1, Beard et al., Virology 75 (1990) 81), ovine, porcine, avian or alternatively simian (for example SAV) origin may be mentioned. Preferably, the adenovirus of animal origin is a canine adenovirus, and more preferably a CAV2 adenovirus [strain Manhattan or A26/61 (ATCC VR-800) for example]. Preferably, adenoviruses of human or canine or mixed origin are used in the context of the invention.

Preferably, the defective adenoviruses of the invention comprise the ITRs, a sequence permitting encapsidation and the nucleic acid of interest. Still more preferably, in the genome of the adenoviruses of the invention, the E1 region at least is non-functional. The viral gene in question may be rendered non-functional by any technique known to a person skilled in the art, and in particular by total elimination, substitution, partial deletion or addition of one or more bases in the gene or genes in question. Such modifications may be obtained in vitro (on the isolated DNA) or in situ, for example by means of genetic engineering techniques, or alternatively by treatment by means of mutagenic agents. Other regions may also be modified, and in particular the E3 region (WO95/02697), E2 region (WO94/28938), E4 region (WO94/28152, WO94/12649, WO95/02697) and L5 region (WO95/02697). According to an especially preferred embodiment, a recombinant adenovirus possessing a deletion of all or part of the E1 and E4 regions is used in the context of the present invention. This type of vector affords, in effect, especially advantageous safety properties.

The defective recombinant adenoviruses according to the invention may be prepared by any technique known to a person skilled in the art (Levrero et al., Gene 101 (1991) 195, EP 185,573; Graham, EMBO J. 3 (1984) 2917). In particular, they may be prepared by homologous recombination between an adenovirus and a plasmid carrying, inter alia, the nucleic acid or cassette of the invention. Homologous recombination takes place after cotransfection of the said adenovirus and said plasmid into a suitable cell line. The cell line used should preferably (i) be amenable to transformation by the said elements, and (ii) contain the sequences capable of complementing the portion of the genome of the defective adenovirus, preferably in integrated form in order to avoid the risks of recombination. As an example of a line, the human embryonic kidney line 293 (Graham et al., J. Gen. Virol. 36 (1977) 59), which contains, in particular, integrated in its genome, the left-hand portion of the genome of an Ad5 adenovirus (12%), may be mentioned. Other lines have been described in Applications Nos. WO94/26914 and WO95/02697).

Thereafter, the adenoviruses which have multiplied are recovered and purified according to standard techniques of molecular biology, as illustrated in the examples.

Regarding adeno-associated viruses (AAV), the latter are relatively small DNA viruses which integrate stably and site-specifically in the genome of the cells they infect. They are capable of infecting a broad spectrum of cells without inducing an effect on growth, morphology or cell differentiation. Moreover, they do not appear to be involved in pathologies in man. The AAV genome has been cloned, sequenced and characterized. It comprises approximately 4700 bases, and contains at each end an inverted repeat region (ITR) of approximately 145 bases serving as origin of replication for the virus. The remainder of the genome is divided into 2 essential regions carrying the encapsidation functions: the left-hand portion of the genome, which contains the rep gene involved in viral replication and expression of the viral genes; and the right-hand portion of the genome, which contains the cap gene coding for the capsid proteins of the virus.

The use of vectors derived from AAV for gene transfer in vitro and in vivo has been described in the literature (see, in particular, WO91/18088; WO93/09239; U.S. Pat. Nos. 4,797,368, 5,139,941, EP 488,528). These applications describe different constructions derived from AAV, in which the rep and/or cap genes are deleted and replaced by a gene of interest, and their use for transferring the said gene of interest in vitro (on cells in culture) or in vivo (directly into a body). The defective recombinant AAVs according to the invention may be prepared by cotransfection, into a cell line infected with a human helper virus (for example an adenovirus), of a plasmid containing the nucleic acid or cassette of the invention flanked by two AAV inverted repeat regions (ITR) and a plasmid carrying the AAV encapsidation genes (rep and cap genes). The recombinant AAV B produced are then purified by standard techniques (see, in particular, WO95/06743).

Regarding herpesviruses and retroviruses, the construction of recombinant vectors has been amply described in the literature: see, in particular, Breakfield et al., New Biologist 3 (1991) 203;

EP 453,242, EP 178,220, Bernstein et al., Genet, Eng. 7 (1985) 235; McCormick, BioTechnology 3 (1985) 689 , and the like. In particular, retroviruses are integrative viruses that selectively infect dividing cells. Hence they constitute vectors of interest for cancer applications. The genome of retroviruses essentially comprises two LTRs, an encapsidation sequence and three coding regions (gag, pol and env). In the recombinant vectors derived from retroviruses, the gag, pol and env genes are generally deleted wholly or partially, and replaced by a heterologous nucleic acid sequence of interest. These vectors may be prepared from different types of retrovirus such as, in particular, MoMuLV (Moloney murine leukaemia virus, also designated MOMLV), MSV (Moloney murine sarcoma virus), HaSV (Harvey sarcoma virus), SNV (spleen necrosis virus), RSV (Rous sarcoma virus) or alternatively Friend virus.

To construct recombinant retroviruses containing the nucleic acid or cassette of the invention, a plasmid containing, in particular, the LTRs, the encapsidation sequence and the nucleic acid or cassette is constructed, and is then used to transfect a so-called encapsidation cell line capable of supplying in trans the retroviral functions which are deficient in the plasmid. Generally, the encapsidation lines are hence capable of expressing the gag, pol and env genes. Such encapsidation lines have been described in the prior art, and in particular the PA317 line (U.S. Pat. No. 4,861,719), the PsiCRIP line (WO90/02806) and the GP+envAm-12 line (WO89/0715). Moreover, the recombinant retroviruses can contain modifications in the LTRs in order to abolish transcriptional activity, as well as extended encapsidation sequences containing a portion of the gag gene (Bender et al., J. Virol. 61 (1987) 1639). The recombinant retroviruses produced are then purified by standard techniques.

To carry out the present invention, it is most especially advantageous to use a defective recombinant adenovirus or retrovirus. These vectors possess, in effect, especially advantageous properties for the transfer of genes coding for apolipoproteins. The adenoviral vectors according to the invention are especially advantageous for a direct administration in vivo of a purified suspension, or for the ex vivo transformation of cells, in particular autologous cells, with a view to their implantation. Furthermore, the adenoviral vectors according to the invention display, in addition, considerable advantages, such as, in particular, their very high efficiency of infection, enabling infections to be produced from small volumes of viral suspension.

In this connection, the invention relates preferentially to a defective recombinant adenovirus comprising, inserted into its genome, a DNA coding for a variant of apolipoprotein A-I as defined above.

According to another especially advantageous embodiment of the invention, a line that produces retroviral vectors containing the sequence coding for the variant of ApoA-I is used for an in vivo implantation. The lines which can be used for this purpose are, in particular, PA317 (U.S. Pat. No. 4,861,719), PsiCrip (WO90/02806) and GP+envAm-12 (U.S. Pat. No. 5,278,056) cells modified to permit the production of a retrovirus containing a nucleic acid sequence coding for a variant of ApoA-I according to the invention.

According to another aspect of the invention, the vector used is a chemical vector. The vector according to the invention can, in effect, be a non-viral agent capable of promoting the transfer of nucleic acids into eukaryotic cells and their expression therein. The chemical or biochemical vectors represent an advantageous alternative to natural viruses, especially on grounds of convenience and safety, and also on account of the absence of theoretical limit regarding the size of the DNA to be transfected.

These synthetic vectors have two main functions, to compact the nucleic acid to be transfected, and to promote its binding to the cell as well as its passage through the plasma membrane and, where appropriate, the two nuclear membranes. To mitigate the polyanionic nature of nucleic acids, the non-viral vectors all possess polycationic charges.

Among the synthetic vectors developed, cationic polymers of polylysine, $(LKLK)_n$, $(LKKL)_n$, polyethylenimine and DEAE-dextran type, or alternatively cationic lipids or lipofectants, are the most advantageous. They possess the property of condensing DNA and of promoting its association with the cell membrane. Among these latter vectors, lipopolyamines (lipofectamine, transfectam, and the like) and different-cationic or neutral lipids (DOTMA, DOGS; DOPE, and the like) may be mentioned. More recently, the concept of receptor-mediated targeted transfection has been developed, which turns to good account the principle of condensing DNA by means of the cationic polymer while directing the binding of the complex to the membrane by means of a chemical coupling between the cationic polymer and the ligand for a membrane receptor, present at the surface of the cell type which it is desired to graft. The targeting of the transferin or insulin receptor or of the asialoglycoprotein receptor of hepatocytes has thus been described.

The invention also relates to any cell genetically modified by insertion of a nucleic acid coding for a variant of apolipoprotein A-I as defined above. Such cells are, advantageously, mammalian cells capable of being administered or implanted in vivo. They can be, in particular, fibroblasts, myoblasts, hepatocytes, keratinocytes, endothelial, epithelial or glial cells, and the like. The cells are preferably of human origin. It is especially advantageous for the cells to be autologous, that is to say removed from a patient, modified ex vivo with a nucleic acid according to the invention for the purpose of endowing them with therapeutic properties, and then readministered to the patient.

The cells according to the invention can originate from primary cultures. They may be removed by any technique known to a person skilled in the art, and then cultured under conditions permitting their proliferation. As regards fibroblasts more especially, these may be readily obtained from biopsies, for example according to the technique described by Ham [Methods Cell. Biol. 21a (1980) 255]. These cells may be used directly for insertion of the nucleic acid of the invention (by means of a viral or chemical vector), or stored, for example by freezing, for the establishment of autologous banks which a view to subsequent use. The cells according to the invention can also be secondary cultures obtained, for example, from pre-established banks (see, for example EP 228,458, EP 289,034, EP 400,047 and EP 456,640).

The cells in culture may, in particular, be infected with the recombinant viruses of the invention in order to endow them with the capacity to produce a variant of apoA-I which is biologically active. The infection is carried out in vitro according to techniques known to a person skilled in the art. In particular, depending on the cell type used and the desired number of copies of virus per cell, a person skilled in the art may adapt the multiplicity of infection and, where appropriate, the number of infection cycles carried out. It is quite obvious that these steps must be performed under suitable conditions of sterility when the cells are intended for an in vivo administration. The-doses of recombinant virus used for infection of the cells may be adapted by a person skilled in the art in accordance with the desired objective. The conditions described above for in vivo administration may be applied to in vitro infection. For infection with retroviruses, it is also possible to coculture the cells which it is desired to infect with cells producing the recombinant retroviruses according to the invention. This enables the need for purification of the retroviruses to be avoided.

Another subject of the invention relates to an implant comprising mammalian cells genetically modified by insertion of a nucleic acid as defined above, and an extracellular matrix. Preferably, the implants according to the invention comprise $10^5$ to $10^{10}$ cells. More preferably, they comprise $10^6$ to $10^8$ thereof. The cells can also be cells producing recombinant viruses containing, inserted into their genome, a nucleic acid as defined above.

More especially, in the implants of the invention, the extracellular matrix comprises a gelling compound and, where appropriate, a support permitting anchoring of the cells.

For the preparation of the implants according to the invention, different types of gelling agent may be employed. The gelling agents are used for inclusion of the cells in a matrix having the constitution of a gel, and to promote anchoring of the cells to the support, where appropriate. Different cellular adhesion agents may hence be used as gelling agents, such as, in particular, collagen, gelatin, glycosaminoglycans, fibronectin, lectins, and the like. Preferably, collagen is used in the context of the present invention. The collagen can be of human, bovine or murine origin. More preferably, type I collagen is used.

As mentioned above, the compositions according to the invention advantageously comprise a support permitting anchoring of the cells. The term anchoring denotes any form of biological and/or chemical and/or physical interaction entailing adhesion and/or binding of the cells to the support. Moreover, the cells may either coat the support used or enter inside this support or both. It is preferable to use, in the context of the invention, a non-toxic and/or biocompatible solid support. In particular, polytetrafluoroethylene (PTFE) fibres or a support of biological origin (coral, bone, collagen, and the like) may be used.

The implants according to the invention may be implanted at different sites of the body. In particular, implantation may be performed in the peritoneal cavity, in the subcutaneous tissue (suprapubic region, iliac or inguinal fossae, and the like), in an organ, a muscle, a tumour or the central nervous system, or alternatively under a mucous membrane. The implants according to the invention are especially advantageous in the sense that they enable release of the apoA-I variant into the body to be controlled. This is determined, in the first place, by the multiplicity of infection and by the number of cells implanted. Thereafter, the release may be controlled either by withdrawal of the implant, which stops the treatment definitively, or by the use of regulable expression systems enabling the expression of the therapeutic genes to be induced or repressed.

As a result of the especially noteworthy anti-atherogenic properties of the variants of the invention, the nucleic acids thus constitute a new medicinal product in the treatment and prevention of cardiovascular pathologies( atherosclerosis, restenosis, and the like).

To this end, the invention relates to any pharmaceutical composition comprising a variant of apolipoprotein A-I and/or a nucleic acid and/or a vector and/or a genetically modified cell as are described above.

The present invention thus affords a new means for the treatment or prevention of pathologies associated with dyslipoproteinaemias, especially in the field of cardiovascular complaints such as myocardial infarction, angina, sudden death, restenosis, cardiac decompensation and stroke. More generally, this approach affords a very promising means of therapeutic intervention for every case in which an apolipoprotein A-I deficiency of a genetic or metabolic nature may be corrected.

The present invention will be described in greater detail by means of the examples which follow, which are to be considered to be illustrative and non-limiting.

4a: Turbidimetry of the association of different ApoAIs and DPMC in the absence of GndHCl (-■-: control; -◆-: recombinant; -◇-: plasma; -□-: Paris.).

4b: Turbidimetry of the association of different ApoAIs and DPMC in the presence of GndHCl (-■-: control; -◆-: recombinant; -◇-: plasma; -□-: Paris.).

4c: Turbidimetry of the association of ApoAI Paris and DPMC (-■-: in the absence of GndHCl; -□-: in the presence of GndHCl (0.5M)).

4d: Turbidimetry of the association of recombinant ApoAI and DPMC (-■-: in the absence of GnHCl; -□-: in the presence of GnHCl (0.5M)).

4e: Turbidimetry of the association of plasma ApoAI and DPMC (-■-: in the absence of GndHCl; -□-: in the presence of GndHCl (0.5M)).

4f: Effect of GndHCl (0.5M) on ApoAI/DPMC association (-■-: in the absence of GndHCl; -□-: in the presence of GndHCl)

Figure 5:
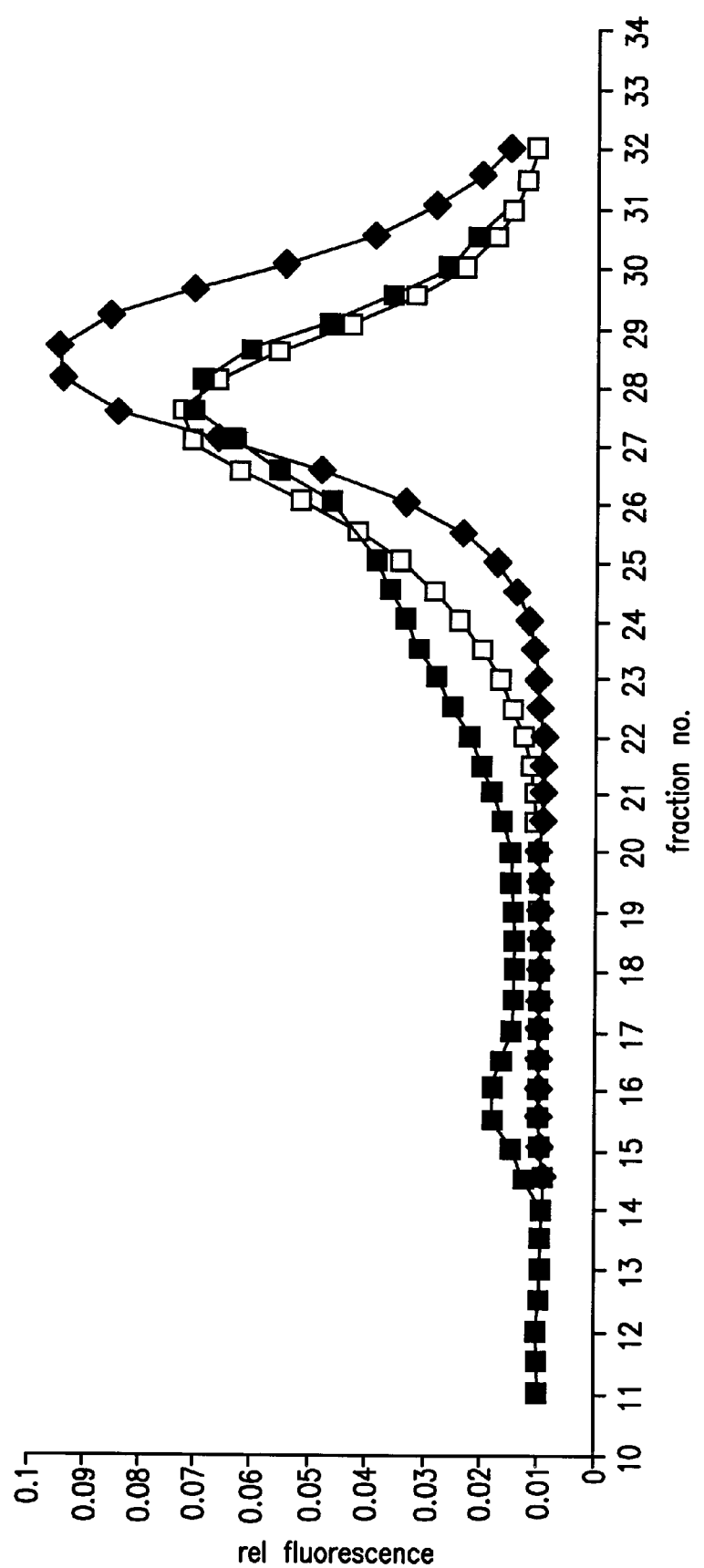

FIG. 5: Relative fluorescence of the Superose 6 PG fractions. (-■-: POPC/AI Paris; -□-: POPC/AI recombinant; -◆-: POPC/AI plasma.)

Figure 6A:
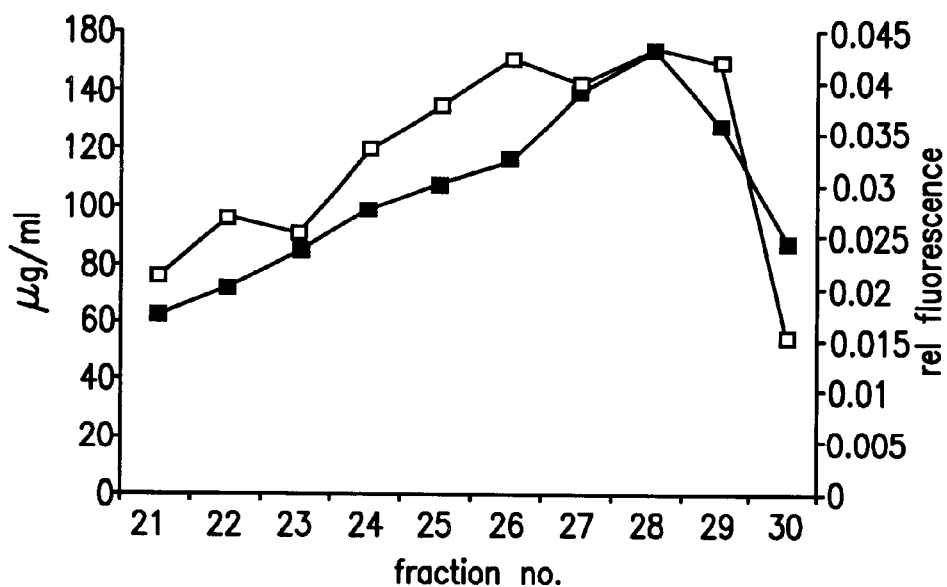
Figure 6B:
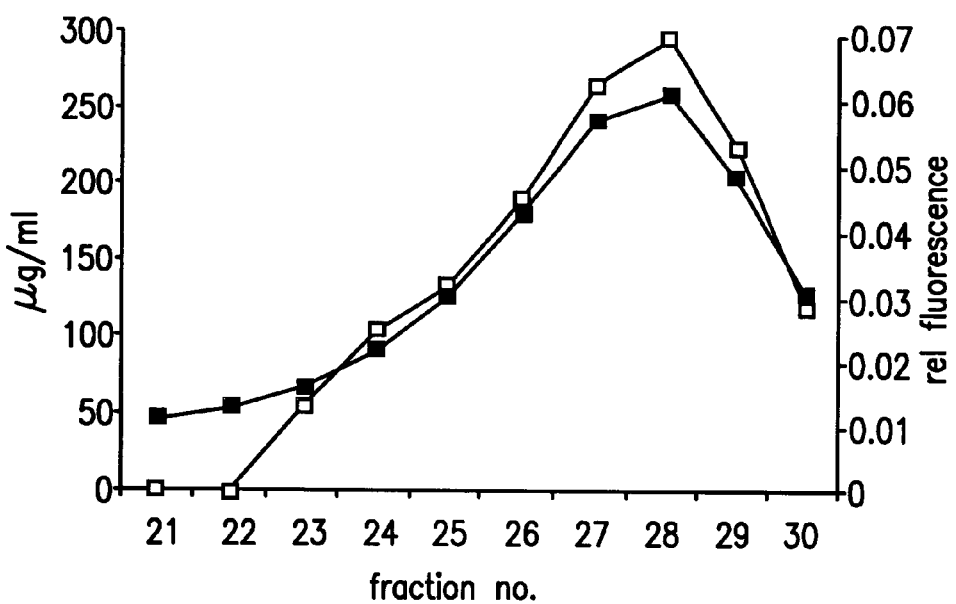

FIGS. 6a–6b: Tryptophan fluorescence and phospholipid concentration for the POPC/AI Paris complex (-■-: relative fluorescence; -□-: phospholipids).

6b: Tryptophan fluorescence and phospholipid concentration for the POPC/recombinant AI complex (-■-: relative fluorescence; -□-: phospholipids).

EXAMPLES

EXAMPLE 1

Demonstration of an ApoA-1 variant

The variant ApoA-1 Paris was identified and isolated from a patient selected as a result of his particular lipid balance. More specifically, the patient displayed the following lipid balance(nature of the sample: serum).

|  |  | Normal |
| --- | --- | --- |
| Total cholesterol | 4.59 mmol/l | 4.54–6.97 |
| Triglycerides | 2.82 mmol/l | 0.74–1.71 |
| HDL cholesterol | 0.25 mmol/l | 0.88–1.60 |
| LDL cholesterol | 3.06 mmol/l | 2.79–4.85 |
| Apolipoprotein A-I | 0.50 g/l | 1.20–2.15 |
| Apolipoprotein B | 1.38 g/l | 0.55–1.30 |
| Phenotype apoE: 3/3 |  |  |

Unexpectedly, this patient displayed no sign of atherosclerosis despite an extremely low concentration of HDL and a hypertriglyceridaemia. This led the Applicants to seek the origin of this protection.

Isolation of HDL Containing ApoA-I Paris from Plasma

After overnight fasting, blood is drawn from subjects carrying the apoA-I Paris gene. The plasma is prepared by slow centrifugation of the blood at 4° C. (2000 g, 30 minutes). The high density lipoproteins are prepared by sequential ultracentrifugation at a density of 1.063–1.21 g/ml (Havel, J. Clin. Invest. 34; 1345–54, 1955). The fraction containing the HDL is then dialysed against 10 mM Tris-HCl buffer, 0.01% sodium azide, pH 7.4.

Demonstration of ApoA-I Paris Dimers

The dialysed HDL fraction is delipidized in a diethyl ether/ethanol (3:1, v/v) mixture, and the protein concentration is estimated by the Lowry method (Lowry et al., J. Biol. Chem., 193: 265–75, 1951). The proteins of the HDL fraction undergo migration on a polyacrylamide gel in the presence of SDS under non-reducing conditions. This migration enables the size of the different proteins of the patient's HDL to be demonstrated. Besides the presence of the proteins corresponding to normal-sized apoA-I and apoA-2, this analysis reveals the presence of higher molecular weight proteins corresponding to apoA-I dimers and complexes of apoA-I and apoA-II. The presence of apoA-I and apoA-II in these complexes was verified by a specific immunological disclosure technique.

Demonstration of the Difference in Charge of the Mutated ApoA-I

The detection of the mutated apoA-I directly on plasma was carried out according to the following protocol (Menzel, H. J., and Utermann, G., Electroforesis, 7: 492–495, 1986): twenty microlitres of plasma are delipidized overnight with an ethanol/ether mixture and resuspended in an application buffer. A 5 μl aliquot undergoes electrophoresis on an isoelectric focusing gel (pH 4–6.5, Pharmolyte), and the proteins are then transferred onto a nylon membrane. The bands corresponding to apoA-I are detected by an immunological reaction using anti-human apoA-I antibody.

The detection of the mutated apoA-I may also be carried out on the HDL proteins. The dialysed HDL fraction is delipidized in a diethyl ether/ethanol (3:1, v/v) mixture, and the protein concentration is estimated by the Lowry method (Lowry et al., J. Biol. Chem., 193:265–75, 1951). Approximately 100 pg of proteins undergo electrophoresis on an isoelectric focusing gel (pH 4–6.5, Pharmolyte), and the proteins are then disclosed by Coomassie blue staining. This technique enables it to be demonstrated that the largest isoforms of the patient's apoA-I having the mutation are shifted towards the anode, which corresponds to a difference in charge of −1 relative to the charge of normal apoA-I.

EXAMPLE 2

Identification of the Gene and the Mutation

The patient's genomic DNA was isolated from the total blood according to the technique of Madisen et al., (Amer. J. Med. Genet, 27: 379–390, 1987). The apoA-I gene was then amplified by the PCR technique. To this end, the amplification reactions were carried out on 1 μg of purified genomic DNA introduced into the following mixture:

10 μl of 10×buffer (100 mM Tris-HCl pH 8.3; 500 mM KCl; 15 mM MgCl$_2$; 0.1% (w/v) gelatin)

10 μl of 2 mM dNTP (DATP, dGTP, dCTP, dTTP)

20. pmol of each primer 2.5 U of Taq polymerase (Perkin-Elmer)

qs 100 μl of H$_2$O

The primers used for the amplification are the following:

Sq5490: 5'-AAGGCACCCCACTCAGCCAGG-3' (SEQ ID No. 3)

Sq5491: 5'-TTCAACATCATCCCACAGGCCTCT-3' (SEQ ID No. 4)

Sq5492: 5'-CTGATAGGCTGGGGCGCTGG-3' (SEQ ID No. 5)

Sq5493: 5'-CGCCTCACTGGGTGTTGAGC-3' (SEQ ID No. 6)

The primers Sq5490 and Sq5491 amplify a 508-bp fragment corresponding to exons 2 and 3 of the apoA-I gene, and the primers Sq5492 and Sq5493 amplify a 664-bp fragment corresponding to exon 4 of this gene.

The amplification products (two PCR fragments of 508 and 664 bp) were then sequenced. To do this, a first method was used, consisting in sequencing directly using the sequencing kit for PCR fragments (Amersham). The primers used for the sequencing are the PCR primers, but it is also possible to use primers internal to the fragments (see primers S4, S6 and S8 below).

A second sequencing technique was also employed, which consisted in cloning the PCR fragments into an M13 mp28 vector. M13 double-stranded DNA was cleaved with EcoRV and then dephosphorylated, and the PCR fragment were treated with Klenow, phosphorylated and ligated to the M13 vector. The clear plaques were then removed and the single-stranded DNA, amplified and thereafter purified on Catalyst (Applied Biosystem), was sequenced with a fluorescent −20 primer (PRISM dye primer kit and Protocol No. 401386, Applied Biosystem), or with primers internal to the fragments after orientations of the latter. The fluorescent dideoxynucleotide technique is then used (DyeDeoxyTerminator kit and Protocol No. 401388, Applied Biosystem).

S8 5'-TGG GAT CGA GTG AAG GAC CTG-3' (SEQ ID No. 7)

S4 5'-CGC CAG AAG CTG CAC CAG CTG-3' (SEQ ID No. 8)

S6 5'-GCG CTG GCG CAG CTC GTC GCT-3' (SEQ ID No. 9)

The sequences originating from several clones were then compiled and compared with the ApoA-I sequence. The amino acid sequence 148 to 154 of mature ApoA-I is given below (corresponding to residues 172–178 in the sequence SEQ ID No. 1).

| ATG | CGC | GAC | CGC | GCG | CGC | GCC | SEQ. ID. NO. 10 |
|-----|-----|-----|-----|-----|-----|-----|-----------------|
| Met | Arg | Asp | Arg 151 | Ala | Arg | Ala | SEQ. ID. NO. 11 |

A C→T mutation in the first base of the codon coding for aa 151, which then codes for a cysteine (see sequence SEQ ID No. 2 below), turned up in a portion of the clones sequenced. This mutation is hence present in the heterozygous state in the patient selected.

| ATG | CGC | GAC | TGC | GCG | CGC | GCC | SEQ. ID. NO. 12 |
|-----|-----|-----|-----|-----|-----|-----|-----------------|
| Met | Arg | Asp | Cys 151 | Ala | Arg | Ala | SEQ. ID. NO. 13 |

The whole of the cDNA coding for the variant apoA-I Paris according to the invention was sequenced. A portion of this sequence is presented in SEQ ID No. 14.

EXAMPLE 3

Construction of a Plasmid Expression Vector (pXL2116mute)

Figure 1:
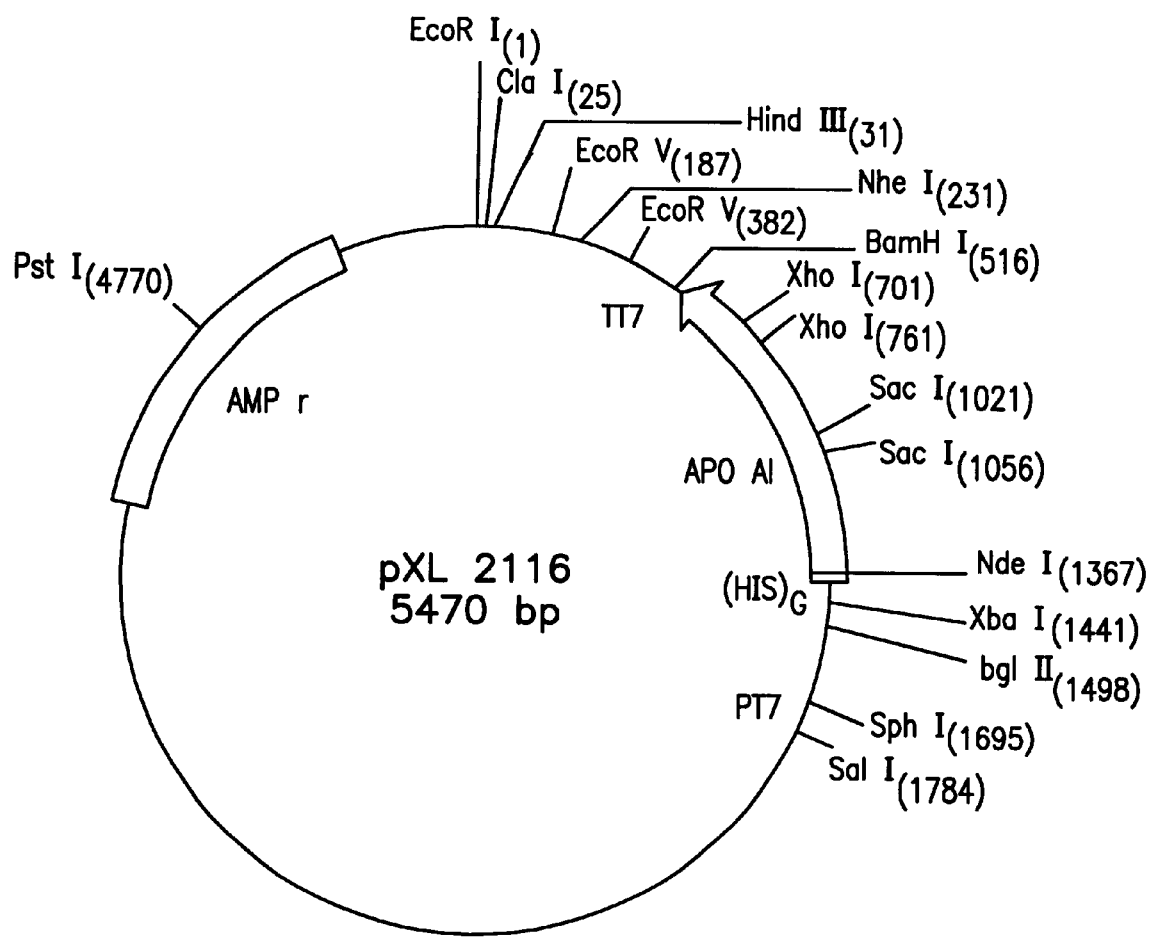
FIG. 1: Restriction map of the plasmid XL2116

ApoA-I Paris possesses a point of mutation located in the sequence of exon 4 of the patient's apoA-I gene. The strategy of construction of the expression vector consists in replacing, in a vector for the expression of apoA-I (the vector pXL2116, FIG. 1), the region corresponding to exon 4 originating from the patient's gene.

3.1. Use of the patient's exon 4 cloned into M13.

Figure 2:
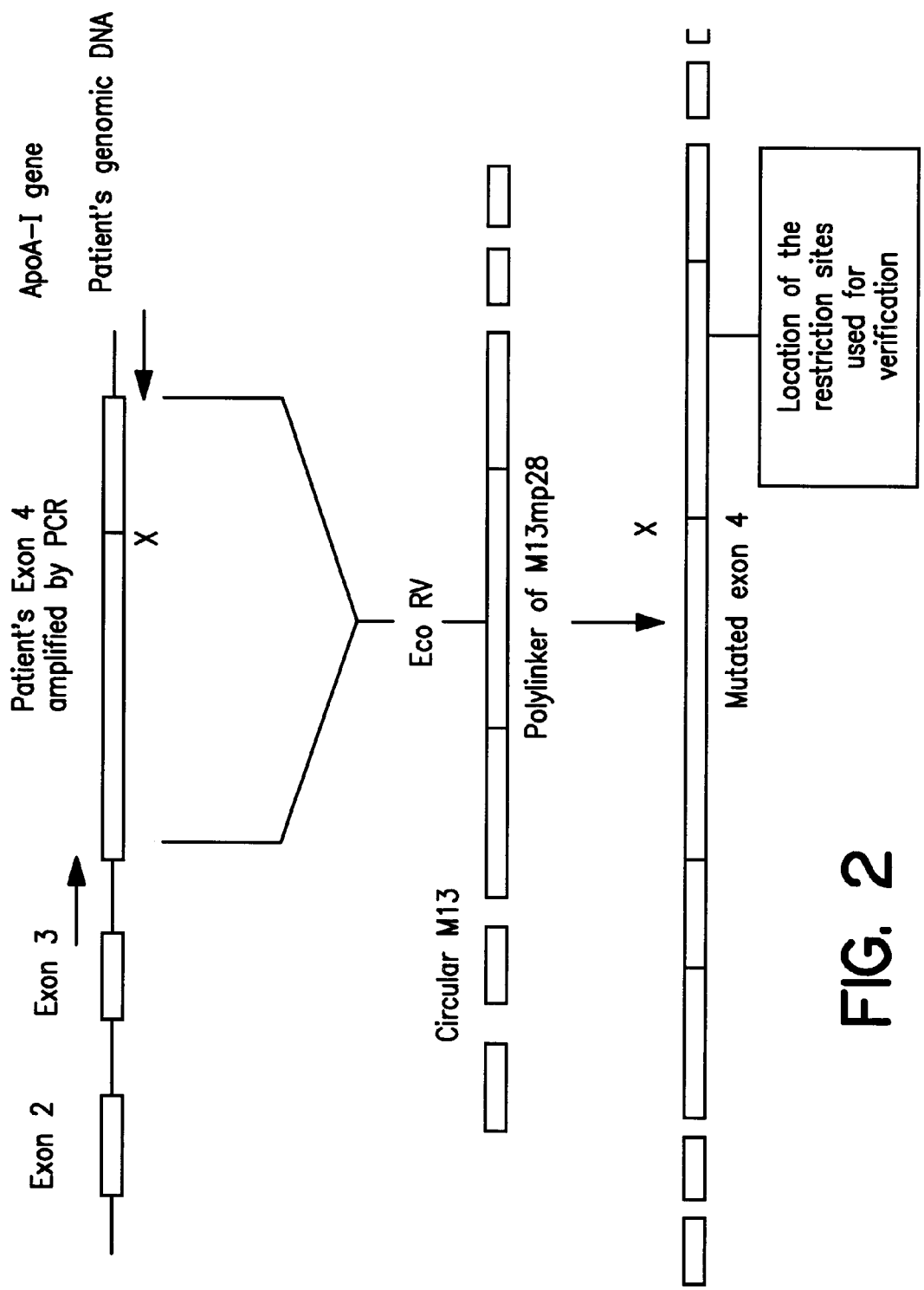
FIG. 2: Construction of the M 13 phage carrying the patient's exon 4.

Exon 4 was produced by PCR from the purified DNA-of the patient's cells, and inserted at the EcoRV site of the polylinker of the phage M13mp28 (FIG. 2).

A mutagenesis by replacement of a fragment of the apoA-I by a fragment originating from M13 carrying the mutation is envisaged. Hence it remains to us to choose the enzymes appropriate to the two vectors so that the latter generate cohesive ends for the vector originating from digested pXL2116 and for the insert originating from digested double-stranded M13.

3.2. Choice of the restriction enzymes

Bsu361 possesses, in M13 and in pXL2116, a unique restriction site upstream of the mutation.

Digestion with BamHI, possessing a unique restriction site at the 3' end of the apoA-I as a result of the cloning technique, and possessing a restriction site in the polylinker of M13, allows us:

1) a ligation of the vector originating from pXL2116 and of the insert originating from M13

2) and this ligation takes place with the incorporation of a fragment of polylinker which will be useful to us for verifying by enzymatic digestion the insertion of the mutated fragment originating from M13.

It should be noted that the presence of this fragment of polylinker in no way alters the apoA-I coding sequence, since it is located after the stop codon.

The histidine-rich polypeptide whose nucleotide sequence has been cloned at the 5' end of the apoA-I will hence be synthesized also.

Figure 3:
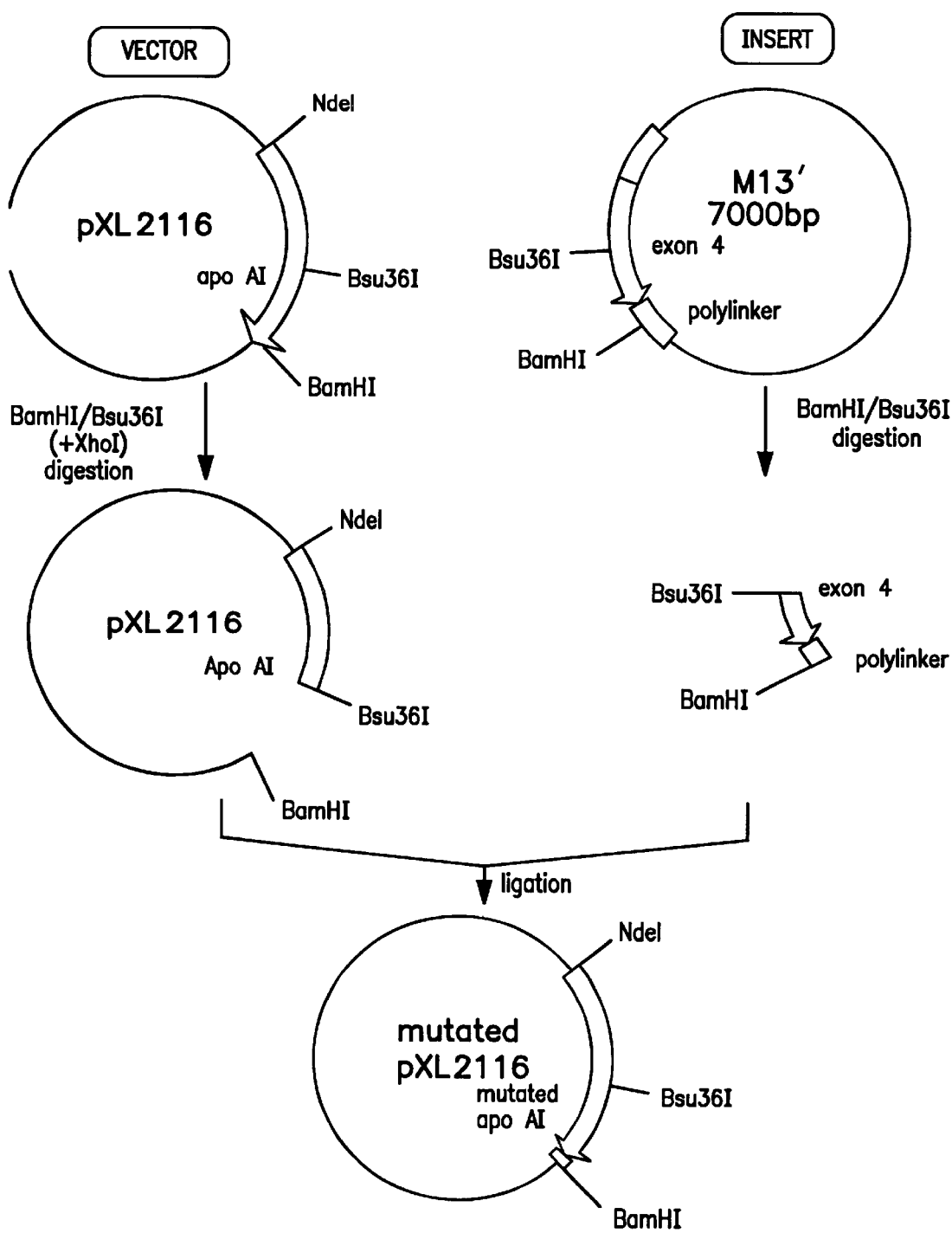
FIG. 3: Construction of the vector carrying mutated PXL2116.
Figure 4A:
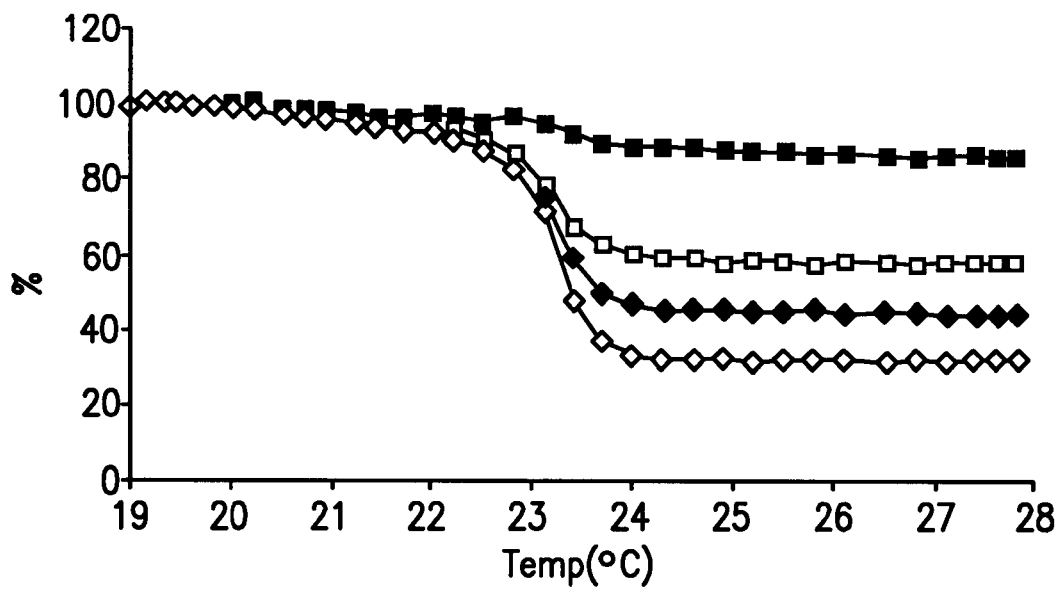
FIGS. 4a–4f: Studies of turbidimetry as a function of temperature.
Figure 4B:
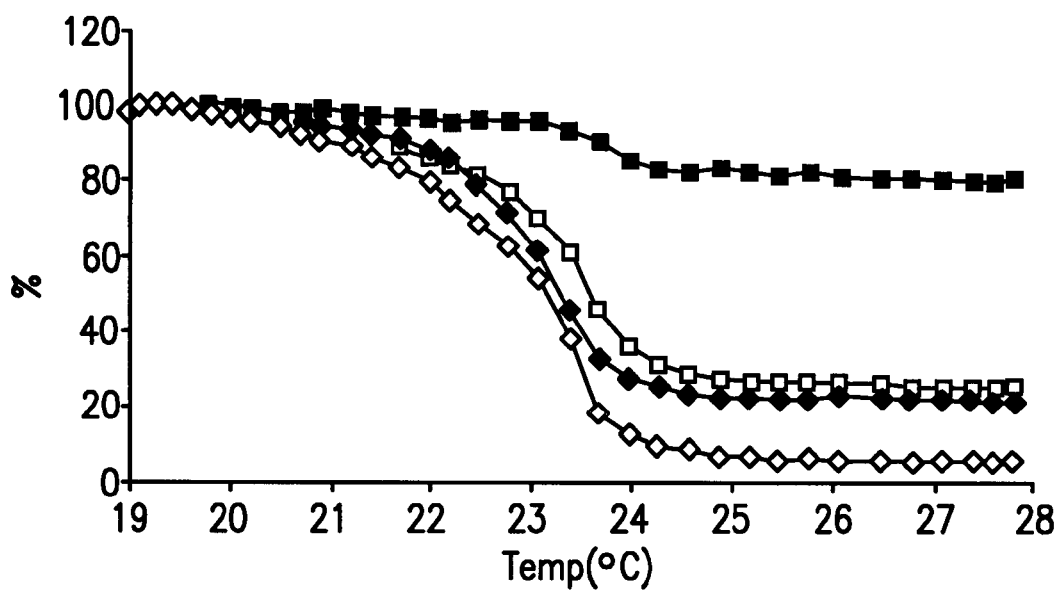
Figure 4C:
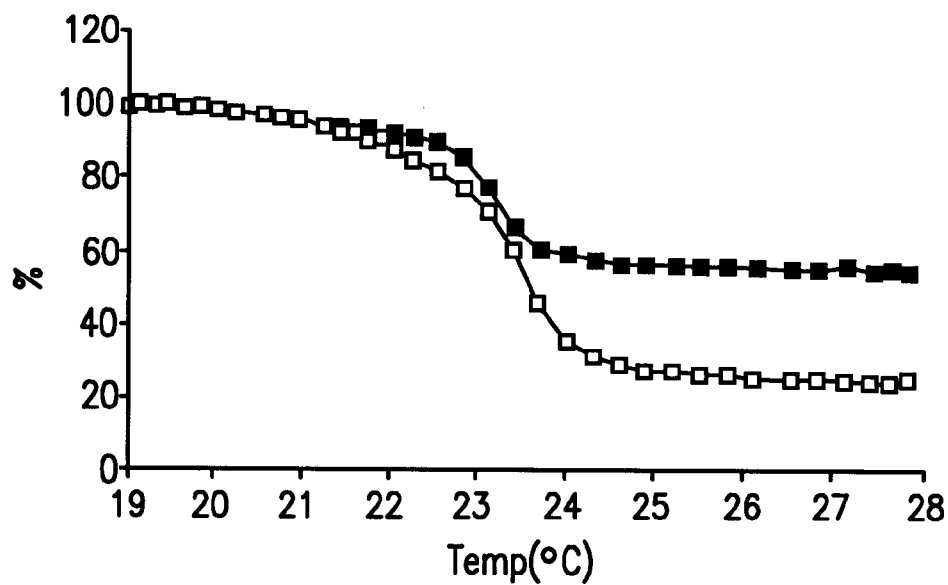
Figure 4D:
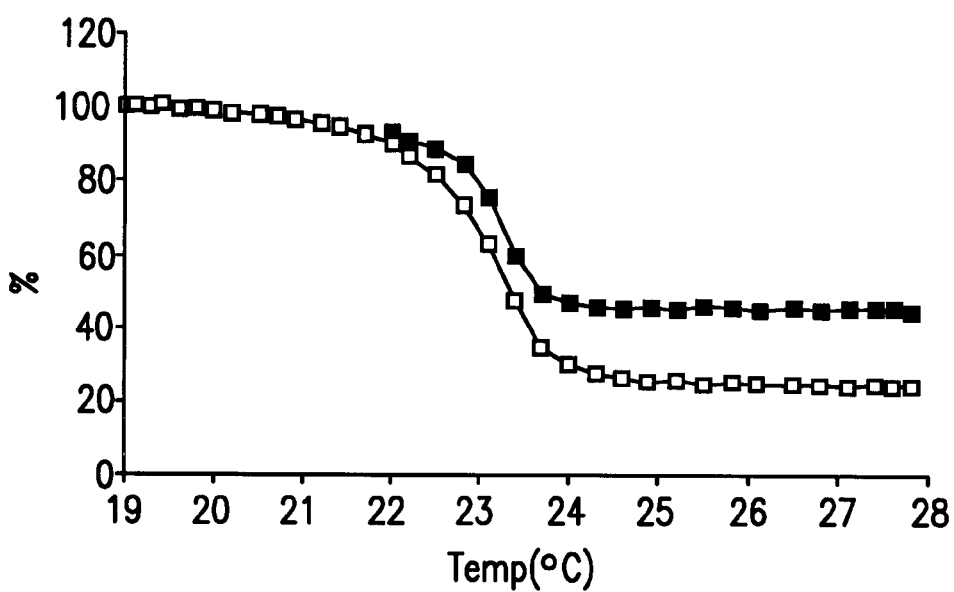
Figure 4E:
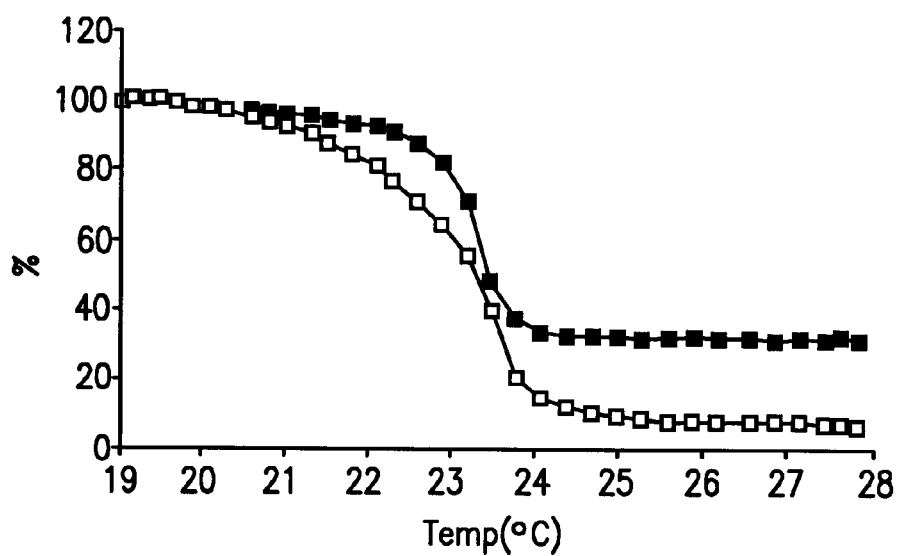
Figure 4F:
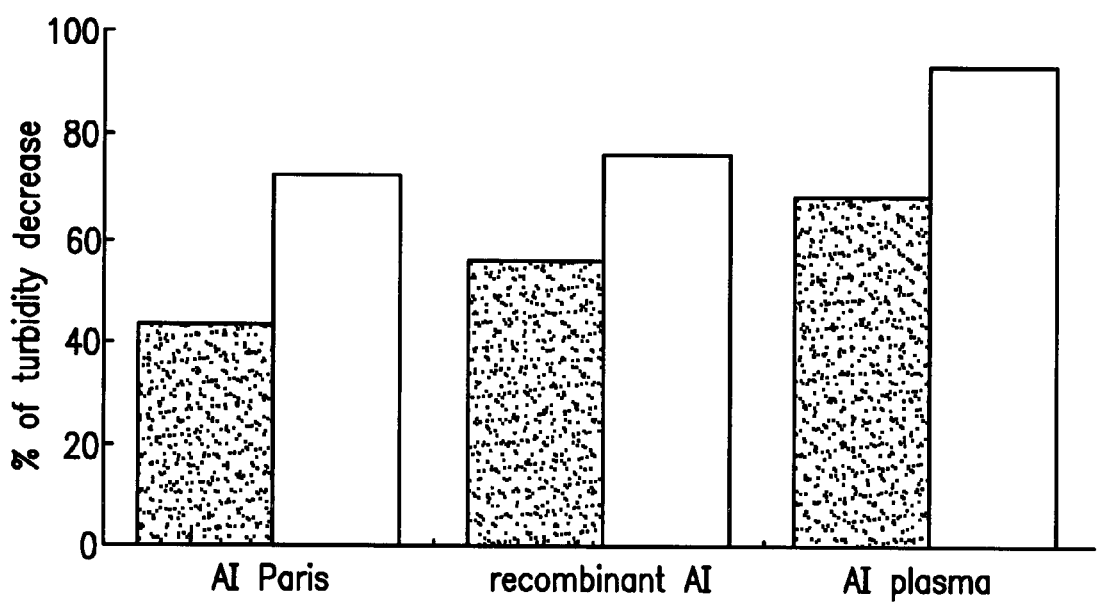

3.3. Construction of the vector (FIG. 3).

M13 rendered double-stranded is digested with Bsu361/BamHI, and the digestion product is applied to gel. The insert thus generated is recovered in a sufficient amount and is indeed 1 Db in size.

pXL2116 is digested with the same enzymes but not purified.

In order to avoid religation of the digestion products, a digestion is performed with XhoI, which recognizes two restriction sites within the Bsu361-BamHI fragment.

In effect, a dephosphorylation was attempted first, but gave very poor results on dishes and no positive clone out of 24 tested.

The optimal amounts of vector and of insert for the ligation were evaluated at 50 ng of vector for 15 ng of insert.

DH5a strains are transformed with the products of the following three ligations:
vector digested with Bsu361 and BamHI without ligase (negative ligation control)
digestion product+ligase
digestion product+insert+ligase The competent cells are also transformed with pUC19 in order to test the efficacy of the transformation.

The results for the cells transformed on dishes of LB medium-with chloramphenicol (selection of BL21 strains) and ampicillin (selection of strains which have integrated the plasmid) are reproduced below.

RESULTS OBTAINED ON PETRI DISHES

| DH5a+ TRANSFORMATION | RESULTS | INTERPRETATION |
|---|---|---|
| pUC19 | 200 clones | Transformation control |
| vector (+fragment) | 0 clone | Complete digestion, no recircularized plasmid |
| vector (+fragment) + ligase | 160 clones | Very large background: strategy of additional digestion largely ineffective |
| vector (+fragment) + ligase + insert | 120 clones | "Diminution effect" of the ligase often noted. The bacteria are not necessarily transformed with a correct mutated sequence |

48 clones are reisolated from dish 4.

In order to identify the positive clones (that is to say those which have inserted the mutated fragment of M13), the plasmid DNA obtained by purification on each of the 48 clones is digested with the enzyme NdeI.

If the insert originating from M13 has indeed been inserted, two fragments will be seen on gel: one of 4.5 kb and one of 1 kb.

If another ligation event has taken place, either several bands will be obtained, or simply one linearized plasmid (general case).

On the basis of the result from the gel, the clones 7, 8, 13, 16 and 26 appear to be correct. The clone which gives a clear result is selected.

In order to verify completely the sequence of the selected clone, six enzymatic digestions are performed.

The presence of the polylinker, and hence of the insert, is verified in this way, but the ligation event must also be verified.

Evidently, the ligation is the expected one, since the size of the plasmid is correct, that is to say equal to that of px12116.

Unless there has been a very rare mutation event, the sequence of the newly cloned apoA-I should be correct.

Hence the clone 8 carries the correctly mutated plasmid px12116.

EXAMPLE 4

Expression of Recombinant ApoA-I Variants

This example describes a method of production of recombinant apoA-I variants. This method was carried out in a bacterium. Other expression systems may be used for this purpose (yeasts, animal cells, and the like).

4.1. Principle

The expression of the plasmid within the bacterium was placed under the control of the T7 promoter and terminator. Isopropyl b-thiogalactopyranoside (IPTG), an inducer of the lactose operon, induces in this system the synthesis of T7 RNA polymerase, which then binds specifically to the T7 promoter and initiates the transcription of the gene for the recombinant protein. The RNA polymerase is stopped by the T7 terminator, thereby preventing the transcriptional flux from spilling over downstream of the sequence of interest.

Rifampicin is an antibiotic that inhibits $E.\ coli$ endogenous RNA polymerase activity. It hence inhibits the synthesis of the bacterial proteins, that is to say both the proteases, thereby limiting the degradations of the protein of interest, and the contaminating bacterial proteins, thereby amplifying the expression of the protein of interest.

4.2. Protocol

The strain used for expression is $Eacherichia\ coli$ BL21 DE3 pLys S. The plasmid DNA is introduced into $E.\ coli$ by transformation according to standard techniques. The culture is stored in the form of the suspension frozen at −20° C. in the presence of 25% glycerol, and aliquoted in 500 µl fractions.

A preculture is initiated by adding a few drops of frozen suspension to 10 ml of M9-ampicillin medium, and then incubated overnight at 37° C. 1-liter conical flasks are inoculated from the preculture and placed in a shaker at 37° C. until an OD of between 0.5 and 1 at 610 nm is obtained. IPTG (Bachem Ref. Q-1280) is then added at a final concentration of 1 mM. After 15 minutes of incubation at 37° C., rifampicin (Sigma) is added at a final concentration of 100 Ag/ml. Then, after 1 hour of culture, the cells are recovered by centrifugation (15 minutes, 8000 rpm) and the expression is verified by electrophoresis under denaturing conditions on a 15% acrylamide gel and by immunoblotting.

The results obtained show that the mutated protein is expressed according to a good level of expression, and that it is, in fact, disclosed with anti-apoA-I polyclonal antibodies.

EXAMPLE 5

Purification of the Recombinant apoA-I variants

This example describes an effective method enabling the recombinant apoA-I variants according to the invention to be purified. It should be understood that other methods may be used.

Since the proteins are expressed in the cytoplasma of *E. coli,* their extraction necessitates, in a first stage, a cell lysis to be performed, followed by a removal of the nucleic acids.

5.1. Bacterial lysis

After centrifugation of the culture, the bacterial pellet is resuspended with gentle stirring in lysis buffer in the presence of protease inhibitors and β-mercaptoethanol.

β-Mercaptoethanol is a reducing agent which cleaves the disulphide bridges formed between two cysteine residues. No disulphide bridge forms in the cytoplasm of *E. coli,* but the presence of a reducing agent proves necessary once the proteins are extracted. In effect, the addition of β-mercaptoethanol to the lysis buffer enables the formation of bridges between the cysteine residues of the bacterial proteins and those of the recombinant proteins to be avoided.

Cell lysis is obtained by 3 times 5 minutes of sonication in ice (Vibracells sonics material, pulsed mode, output control 5); it is followed by a centrifugation at 10,000 rpm (1 hour, 4° C. on Beckman J2-21 M/E, JA10 rotor) enabling cell debris to be removed. A protein assay is carried out on the supernatant by the Bradford colorimetric method.

5.2. Precipitation of nucleic acids

This is carried out on the lysis supernatant with a 10% solution of streptomycin sulphate in the proportion of 10 ml for 10 g of proteins, with gentle magnetic stirring for 1 hour at 4° C. The nucleic acids are removed by centrifugation at 10,000 rpm (1 hour, 4° C. on Beckman J2–21 M/E, JA10 rotor), and the protein concentration of the supernatant is evaluated by calorimetric assay.

At the end of these two steps, a protein solution of known concentration is obtained in which all of the intracellular proteins, including the protein of interest, are present together. The latter is purified by chromatographic techniques.

Chromatography by gel filtration

Affinity chromatography 5.3. Chromatography by gel filtration

The object of this step is to remove the EDTA, a molecule that interferes with the conditions required for the affinity chromatography. For this purpose, the support Tris-acryl GF 05 (Sepracor) was selected. This gel permits the separation of molecules whose molecular mass (MM) is between 300 and 2500 daltons, and the exclusion of molecules of MM above 2500 daltons, including proteins. This gel has, moreover, the advantage of possessing good resistance to pressure, making it possible to work at a high flow rate without modifying the resolution. Chromatography of the bacterial lysate is carried out in pH 8 phosphate buffer. The protein concentration in the exclusion volume is determined and, where appropriate, adjusted to 4 mg/ml by dilution in the pH 8 phosphate buffer.

This step may be replaced by a dialysis against 2×10 liters of PBS. The protein solution is then exposed to 25 mM Hecameg, this detergent favouring the next step of purification by decreasing protein-protein interactions.

5.4. Affinity chromatography Principle

The presence of 6 consecutive histidine residues associated with the recombinant protein endows it with an especially high affinity for nickel ions ($Ni^{2+}$) (15). These $Ni^{2+}$ ions are bound to an agarose matrix by means of nitriloacetic acid (NTA). Between the imidazole of the histidines and the nickel ions, a metal chelation bond is produced; this bond is stronger than an ionic bond and weaker than a covalent bond.

Protocol

The binding capacity of the NiNTA-agarose gel (Qiagen) is 2 mg of protein per ml of gel. This gel is equilibrated in pH 8 buffer with the addition of 25 mM Hecameg. The contaminating bacterial proteins are non-retained at pH 8, or removed at pH 6, and the protein of interest is recovered at pH 5. These steps are carried out in the presence of 25 mM Hecameg.

The fractions (2 ml) eluted at pH 5 are treated with:

60 µl of 1M NaOH (neutralization)

10 µl of 0.2M PMSF

40 µl of 0.1M EDTA

The fractions are pooled in accordance with the concentration and purity of the eluted protein. These characteristics are analysed by electrophoresis (15% SDS-PAGE).

Elution at pH 5 detaches the protein associated with the nickel by acting on the $Ni^{2+}$-NTA bond. Hence it is necessary to dissociate this cation from the recombinant protein. This step is performed by competition by means of an incubation with gentle magnetic stirring at 4° C. for 1 hour in the presence of 50 mM histidine.

5.5. Dialyses

This enables the histidine and the nickel to be removed. The sample is dialysed (Spectra/Por membrane, MWCO 12–14,000 daltons) at 4° C. for 5 hours, and then overnight against 2 times 10 liters of 2 mM EDTA-PBS buffer. A protein assay is finally performed.

This method enables the apoA-I Paris protein to be obtained in purified form essentially free from contaminating proteins.

EXAMPLE 6

Physicochemical Properties of Recombinant ApoA-I Paris and Recombinant Normal ApoA-I 6.1. Turbidimetry measurements 2.0 6.1.1. Turbidimetry as a function of temperature Measurement of the absorbance of DMPC vesicles at 325 nm in the presence of apoA-I is a measure of the formation of small-sized discoidal proteolipid complexes. Temperature variation analysis between 19 and 28° C. shows us a decrease in the absorbance around the transition temperature of the phospholipids (23° C.), testifying to the formation of complexes. FIG. 4 (in the presence or absence of GdnHDL in order to avoid dimer formation) shows the comparison of the formation of these complexes with the recombinant normal apoA-I and recombinant apoA-I Paris, as well as native apoA-I. These three proteins have fairly similar behaviours but, with for apoA-I Paris, a tendency is noted to associate with itself to form diners.

6.1.2. Turbidimetry as a function of time

The fall in turbidimetry of DMPC vesicles after incubation of the apoA-I molecules was followed at a given temperature as a function of time in the presence or absence of GdnHDL. The time constant (1/t1/2, which corresponds to a 50% fall in the initial turbidimetry) is evaluated as a function of 1/T (temperature in Kelvin). The rate of association is rapid for native apoA-I, and slower for the recombinant apoA-I molecules, in particular apoA-I Paris. Moreover, the addition of GdnHDL increases the protein-lipid association. This occurs very noticeably in the case of the recombinant apoA-I molecules, in particular apoA-I Paris.

6.2. Tryptophan fluorescence emission spectrum

The fluorescence emission spectrum of the tryptophans in the different apoA-I molecules was measured at wavelengths between 300 and 400 nm (excitation at 295 nm). The emission maxima are shown in Table 1 below for the apoA-I molecules and for the apoA-I/cholesterol/POPC complexes. The fluorescence emission maxima of the tryptophans in the different apoA-I molecules and complexes are identical, indicating that the tryptophans are in the same environment in all three proteins.

TABLE 1

| Product | Emission maximum |
|---|---|
| A-I Paris | 335 |
| POPC/C/A-I Paris | 332 |
| Recombinant A-I | 334 |
| POPC/C/A-I rec | 332 |
| A-I plasma | 336 |
| POPC/C/A-I plasma | 333 |

6.3. Isolation and characterization of the apoA-I/lipid complexes

Complexes with apoA-I and POPC were prepared by the cholate technique. The complexes were separated from free apoA-I by gel filtration chromatography on a Superose 6PG column, and their compositions analysed. The gel filtration profiles are shown in FIG. 5. A single homogeneous peak is obtained for the complexes made with native apoA-I whereas, with the recombinant apoA-I molecules, heterogeneous populations are observed. The free apoA-I molecules are eluted in fractions 20 to 24. The phospholipid concentrations and the tryptophan fluorescence in each fraction for the different complexes are shown in FIG. 6.

EXAMPLE 7

Construction of an Adenoviral Vector for Expression of the Mutated ApoA-I

A cDNA coding for a variant according to the invention containing the Arg→Cys mutation at position 151 of the mature ApoA-I is obtained by PCR.
The Primers
   AIm1: ATC GAT ACC GCC ATG AAA GCT GCG GTG CTG (SEQ ID No. 16),
   AIm2: ATG GGC GCG CGC GCA GTC GCG CAT CTC CTC (SEQ ID No. 17),
   AIm3: GAG GAG ATG CGC GAC TGC GCG CGC GCC CAT (SEQ ID No. 18)
and AIm4: GTC GAC GGC GCC TCA CTG GGT GTT GAG CTT (SEQ ID No. 19)
   are used. The primers AIm1 and AIm4 introduce ClaI and SalI sites, respectively, at the 5' and 3' ends of the cDNA, while the primers AIm2 and AIm3, which are complementary, introduce the mutation. PCR reactions with the primer pairs AIm1-AIm2 and AIm3-AIm4 are first performed on a cDNA of the unmutated ApoA-I. The fragments originating from these PCRs are then reintroduced into a third PCR in the presence of the primers AIm1 and AIm4, generating an 822-bp fragment which is then cloned into pCRII (Invitrogen) for verification of its sequence. The ClaI-SalI fragment which contains the mutated cDNA is then introduced via the same restriction sites into the shuttle vector pXL-RSV-LPL, which contains LPL cDNA under the control of an RSV LTR promoter and with a polyadenylation site of bovine growth hormone, replacing the LPL cDNA (FR94/06759). Any other shuttle vector may obviously be used. The resulting vector is then linearized and cotransfected into 293 to obtain the recombinant adenoviruses. The adenoviruses thereby obtained may be amplified on plaques, purified (in particular with caesium chloride) and then stored frozen, for example in glycerol. For their therapeutic use, they may be combined with any pharmaceutically acceptable vehicle. Such vehicles can be, in particular, sterile, isotonic saline solutions (containing monosodium or disodium phosphate, sodium, potassium, calcium or magnesium chloride, and the like, or mixtures of such salts), or dry, in particular lyophilized compositions which, on addition of sterilized water or of physiological saline, as appropriate, enable injectable solutions to be made up. In their use for the treatment of pathologies associated with dyslipoproteinaemias, the defective recombinant adenoviruses according to the invention may be administered according to different modes, and in particular by intravenous injection. Preferably, they are injected into the portal vein. The doses of virus used for the injection may be adapted in accordance with different parameters, and in particular in accordance with the mode of administration used, the pathology in question or alternatively the desired treatment period. Generally speaking, the recombinant viruses according to the invention are formulated and administered in the form of doses of between $10^4$ and $10^{14}$ pfu/ml. For AAVs and adenoviruses, doses of $10^6$ to $10^{10}$ pfu/ml may also be used. The term pfu ("plaque forming unit") corresponds to the infectious power of a suspension of virions, and is determined by infecting a suitable cell culture and measuring, generally after 48 hours, the number of plaques of infected cells. The techniques of determination of the pfu titre of a viral solution are well documented in the literature.

What is claimed is:

1. A purified apolipoprotein A-I comprising a wild type or natural variant mature human apolipoprotein A-I amino acid sequence modified by a conversion of a wild type amino acid sequence Met-Arg-Asp-Arg-Ala-Arg-Ala (SEQ ID No. 11) to Met-Arg-Asp-Cys-Ala-Arg-Ala (SEQ ID No. 13), wherein the purified apolipoprotein A-I forms a dimer in plasma.

2. The purified apolipoprotein A-I of claim 1, wherein the wild type or natural variant mature human apolipoprotein A-I amino acid sequence is farther modified by substitution, deletion or addition of at least one amino acid, and the further modification does not eliminate the activity of the purified apolipoprotein A-I as measured by a cholesterol efflux test.

3. The purified apolipoprotein A-I of claim 2, wherein the further modification comprises a substitution of cysteine for another amino acid or addition of a cysteine.

4. The purified apolipoprotein A-I of claim 1 containing a peptide sequence of residues 68 to 267 of SEQ ID No. 2 with residue 175 being replaced by a cysteine.

5. A nucleic acid coding for the purified apolipoprotein A-I of claim 1.

6. The nucleic acid of claim 5, which is a cDNA.

7. A nucleic acid coding for the purified apolipoprotein A-I of claim 2.

8. The nucleic acid of claim 7, which is a cDNA.

9. A nucleic acid coding for the purified apolipoprotein A-I of claim 3.

10. The nucleic acid of claim 9, which is a cDNA.

11. A nucleic acid coding for the purified apolipoprotein A-I of claim 10.

12. The nucleic acid of claim 11, which is a cDNA.

13. A cell genetically modified to express the purified apolipoprotein A-I of claim 1.

14. The cell of claim 13, wherein the cell is a mammalian cell.

15. A composition comprising the cell of claim 14 and an extracellular matrix.

16. A vector comprising a nucleic acid according to claim 5.

17. The vector of claim 16, which is a selected from the group consisting of a viral vector and a chemical vector.

18. A vector comprising a nucleic acid according to claim 7.

19. The vector of claim 18, which is a selected from the group consisting of a viral vector and a chemical vector.

20. A vector comprising a nucleic acid according to claim 9.

21. The vector of claim 20, which is a selected from the group consisting of a viral vector and a chemical vector.

22. A vector comprising a nucleic acid according to claim 11.

23. The vector of claim 22, which is a selected from the group consisting of a viral vector and a chemical vector.

* * * * *

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
       (A) LENGTH: 842 base pairs
       (B) TYPE: nucleic acid
       (C) STRANDEDNESS: double
       (D) TOPOLOGY: linear (ii) MOLECULE TYPE: cDNA (ix) FEATURE:
    (A) NAME/KEY: CDS
    (B) LOCATION: 1..804

(xi) SEQUENCE DESCRIPTION: SEQ ID NO:1:

```
ATG AAA GCT GCG GTG CTG ACC TTG GCC GTG CTC TTC CTG ACG GGG AGC         48
Met Lys Ala Ala Val Leu Thr Leu Ala Val Leu Phe Leu Thr Gly Ser
 1               5                  10                  15

CAG GCT CGG CAT TTC TGG CAG CAA GAT GAA CCC CCC CAG AGC CCC TGG         96
Gln Ala Arg His Phe Trp Gln Gln Asp Glu Pro Pro Gln Ser Pro Trp
                20                  25                  30

GAT CGA GTG AAG GAC CTG GCC ACT GTG TAC GTG GAT GTG CTC AAA GAC        144
Asp Arg Val Lys Asp Leu Ala Thr Val Tyr Val Asp Val Leu Lys Asp
             35                  40                  45

AGC GGC AGA GAC TAT GTG TCC CAG TTT GAA GGC TCC GCC TTG GGA AAA        192
Ser Gly Arg Asp Tyr Val Ser Gln Phe Glu Gly Ser Ala Leu Gly Lys
         50                  55                  60

CAG CTA AAC CTA AAG CTC CTT GAC AAC TGG GAC AGC GTG ACC TCC ACC        240
Gln Leu Asn Leu Lys Leu Leu Asp Asn Trp Asp Ser Val Thr Ser Thr
 65                  70                  75                  80

TTC AGC AAG CTG CGC GAA CAG CTC GGC CCT GTG ACC CAG GAG TTC TGG        288
Phe Ser Lys Leu Arg Glu Gln Leu Gly Pro Val Thr Gln Glu Phe Trp
                 85                  90                  95

GAT AAC CTG GAA AAG GAG ACA GAG GGC CTG AGG CAG GAG ATG AGC AAG        336
Asp Asn Leu Glu Lys Glu Thr Glu Gly Leu Arg Gln Glu Met Ser Lys
                100                 105                 110

GAT CTG GAG GAG GTG AAG GCC AAG GTG CAG CCC TAC CTG GAC GAC TTC        384
Asp Leu Glu Glu Val Lys Ala Lys Val Gln Pro Tyr Leu Asp Asp Phe
            115                 120                 125

CAG AAG AAG TGG CAG GAG GAG ATG GAG CTC TAC CGC CAG AAG GTG GAG        432
Gln Lys Lys Trp Gln Glu Glu Met Glu Leu Tyr Arg Gln Lys Val Glu
        130                 135                 140

CCG CTG CGC GCA GAG CTC CAA GAG GGC GCG CGC CAG AAG CTG CAC GAG        480
Pro Leu Arg Ala Glu Leu Gln Glu Gly Ala Arg Gln Lys Leu His Glu
145                 150                 155                 160

CTG CAA GAG AAG CTG AGC CCA CTG GGC GAG GAG ATG CGC GAC CGC GCG        528
Leu Gln Glu Lys Leu Ser Pro Leu Gly Glu Glu Met Arg Asp Arg Ala
                165                 170                 175

CGC GCC CAT GTG GAC GCG CTG CGC ACG CAT CTG GCC CCC TAC AGC GAC        576
Arg Ala His Val Asp Ala Leu Arg Thr His Leu Ala Pro Tyr Ser Asp
            180                 185                 190

GAG CTG CGC CAG CGC TTG GCC GCG CGC CTT GAG GCT CTC AAG GAG AAC        624
Glu Leu Arg Gln Arg Leu Ala Ala Arg Leu Glu Ala Leu Lys Glu Asn
        195                 200                 205

GGC GGC GCC AGA CTG GCC GAG TAC CAC GCC AAG GCC ACC GAG CAT CTG        672
Gly Gly Ala Arg Leu Ala Glu Tyr His Ala Lys Ala Thr Glu His Leu
    210                 215                 220

AGC ACG CTC AGC GAG AAG GCC AAG CCC GCG CTC GAG GAC CTC CGC CAA        720
Ser Thr Leu Ser Glu Lys Ala Lys Pro Ala Leu Glu Asp Leu Arg Gln
225                 230                 235                 240

GGC CTG CTG CCC GTG CTG GAG AGC TTC AAG GTC AGC TTC CTG AGC GCT        768
Gly Leu Leu Pro Val Leu Glu Ser Phe Lys Val Ser Phe Leu Ser Ala
                245                 250                 255

CTC GAG GAG TAC ACT AAG AAG CTC AAC ACC CAG TGA GGCGCCCGCC            814
Leu Glu Glu Tyr Thr Lys Lys Leu Asn Thr Gln  *
                260                 265

GCCGCCCCC TTCCCGGTGC TCAGAATA                                          842
```

(2) INFORMATION FOR SEQ ID NO:2:

(i) SEQUENCE CHARACTERISTICS:
        (A) LENGTH: 267 amino acids
        (B) TYPE: amino acid
        (D) TOPOLOGY: linear (ii) MOLECULE TYPE: protein (xi) SEQUENCE DESCRIPTION: SEQ ID NO:2:

```
Met Lys Ala Ala Val Leu Thr Leu Ala Val Leu Phe Leu Thr Gly Ser
 1               5                  10                  15

Gln Ala Arg His Phe Trp Gln Gln Asp Glu Pro Pro Gln Ser Pro Trp
                20                  25                  30

Asp Arg Val Lys Asp Leu Ala Thr Val Tyr Val Asp Val Leu Lys Asp
            35                  40                  45

Ser Gly Arg Asp Tyr Val Ser Gln Phe Glu Gly Ser Ala Leu Gly Lys
        50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Glu Met Glu Leu Tyr Arg Gln Lys Val Glu
130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln
            260                 265
```

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

AAGGCACCCC ACTCAGCCAG G        21

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

TTCAACATCA TCCCACAGGC CTCT                       24

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

CTGATAGGCT GGGGCGCTGG                            20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

CGCCTCACTG GGTGTTGAGC                            20

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

TGGGATCGAG TGAAGGACCT G                         21

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

CGCCAGAAGC TGCACCAGCT G                         21

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

GCGCTGGCGC AGCTCGTCGC T                              21

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..21

(xi) SEQUENCE DESCRIPTION: SEQ ID NO:10:

ATG CGC GAC CGC GCG CGC GCC                        21
Met Arg Asp Arg Ala Arg Ala
  270             275

(2) INFORMATION FOR SEQ ID NO:11:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO:11:

Met Arg Asp Arg Ala Arg Ala
  1             5

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..21

(xi) SEQUENCE DESCRIPTION: SEQ ID NO:12:

ATG CGC GAC TGC GCG CGC GCC                        21
Met Arg Asp Cys Ala Arg Ala
  270             275

(2) INFORMATION FOR SEQ ID NO:13:

(i) SEQUENCE CHARACTERISTICS:
        (A) LENGTH: 7 amino acids
        (B) TYPE: amino acid
        (D) TOPOLOGY: linear -continued (ii) MOLECULE TYPE: protein (xi) SEQUENCE DESCRIPTION: SEQ ID NO:13:

```
Met Arg Asp Cys Ala Arg Ala
 1               5
```

(2) INFORMATION FOR SEQ ID NO:14:

(i) SEQUENCE CHARACTERISTICS:
        (A) LENGTH: 603 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..603

(xi) SEQUENCE DESCRIPTION: SEQ ID NO:14:

```
CTA AAG CTC CTT GAC AAC TGG GAC AGC GTG ACC TCC ACC TTC AGC AAG      48
Leu Lys Leu Leu Asp Asn Trp Asp Ser Val Thr Ser Thr Phe Ser Lys
         10                  15                  20

CTG CGC GAA CAG CTC GGC CCT GTG ACC CAG GAG TTC TGG GAT AAC CTG      96
Leu Arg Glu Gln Leu Gly Pro Val Thr Gln Glu Phe Trp Asp Asn Leu
     25                  30                  35

GAA AAG GAG ACA GAG GGC CTG AGG CAG GAG ATG AGC AAG GAT CTG GAG     144
Glu Lys Glu Thr Glu Gly Leu Arg Gln Glu Met Ser Lys Asp Leu Glu
 40                  45                  50                  55

GAG GTG AAG GCC AAG GTG CAG CCC TAC CTG GAC GAC TTC CAG AAG AAG     192
Glu Val Lys Ala Lys Val Gln Pro Tyr Leu Asp Asp Phe Gln Lys Lys
                 60                  65                  70

TGG CAG GAG GAG ATG GAG CTC TAC CGC CAG AAG GTG GAG CCG CTG CGC     240
Trp Gln Glu Glu Met Glu Leu Tyr Arg Gln Lys Val Glu Pro Leu Arg
             75                  80                  85

GCA GAG CTC CAA GAG GGC GCG CGC CAG AAG CTG CAC GAG CTG CAA GAG     288
Ala Glu Leu Gln Glu Gly Ala Arg Gln Lys Leu His Glu Leu Gln Glu
         90                  95                 100

AAG CTG AGC CCA CTG GGC GAG GAG ATG CGC GAC TGC GCG CGC GCC CAT     336
Lys Leu Ser Pro Leu Gly Glu Glu Met Arg Asp Cys Ala Arg Ala His
     105                 110                 115

GTG GAC GCG CTG CGC ACG CAT CTG GCC CCC TAC AGC GAC GAG CTG CGC     384
Val Asp Ala Leu Arg Thr His Leu Ala Pro Tyr Ser Asp Glu Leu Arg
120                 125                 130                 135

CAG CGC TTG GCC GCG CGC CTT GAG GCT CTC AAG GAG AAC GGC GGC GCC     432
Gln Arg Leu Ala Ala Arg Leu Glu Ala Leu Lys Glu Asn Gly Gly Ala
                140                 145                 150

AGA CTG GCC GAG TAC CAC GCC AAG GCC ACC GAG CAT CTG AGC ACG CTC     480
Arg Leu Ala Glu Tyr His Ala Lys Ala Thr Glu His Leu Ser Thr Leu
            155                 160                 165

AGC GAG AAG GCC AAG CCC GCG CTC GAG GAC CTC CGC CAA GGC CTG CTG     528
Ser Glu Lys Ala Lys Pro Ala Leu Glu Asp Leu Arg Gln Gly Leu Leu
        170                 175                 180

CCC GTG CTG GAG AGC TTC AAG GTC AGC TTC CTG AGC GCT CTC GAG GAG     576
Pro Val Leu Glu Ser Phe Lys Val Ser Phe Leu Ser Ala Leu Glu Glu
    185                 190                 195

TAC ACT AAG AAG CTC AAC ACC CAG TGA                                 603
Tyr Thr Lys Lys Leu Asn Thr Gln  *
200                 205
```

(2) INFORMATION FOR SEQ ID NO:15:

(i) SEQUENCE CHARACTERISTICS:
        (A) LENGTH: 200 amino acids
        (B) TYPE: amino acid
        (D) TOPOLOGY: linear (ii) MOLECULE TYPE: protein (xi) SEQUENCE DESCRIPTION: SEQ ID NO:15:

```
Leu Lys Leu Leu Asp Asn Trp Asp Ser Val Thr Ser Thr Phe Ser Lys
 1               5                  10                  15

Leu Arg Glu Gln Leu Gly Pro Val Thr Gln Glu Phe Trp Asp Asn Leu
                20                  25                  30

Glu Lys Glu Thr Glu Gly Leu Arg Gln Glu Met Ser Lys Asp Leu Glu
            35                  40                  45

Glu Val Lys Ala Lys Val Gln Pro Tyr Leu Asp Asp Phe Gln Lys Lys
    50                  55                  60

Trp Gln Glu Glu Met Glu Leu Tyr Arg Gln Lys Val Glu Pro Leu Arg
65                  70                  75                  80

Ala Glu Leu Gln Glu Gly Ala Arg Gln Lys Leu His Glu Leu Gln Glu
                85                  90                  95

Lys Leu Ser Pro Leu Gly Glu Glu Met Arg Asp Cys Ala Arg Ala His
                100                 105                 110

Val Asp Ala Leu Arg Thr His Leu Ala Pro Tyr Ser Asp Glu Leu Arg
            115                 120                 125

Gln Arg Leu Ala Ala Arg Leu Glu Ala Leu Lys Glu Asn Gly Gly Ala
    130                 135                 140

Arg Leu Ala Glu Tyr His Ala Lys Ala Thr Glu His Leu Ser Thr Leu
145                 150                 155                 160

Ser Glu Lys Ala Lys Pro Ala Leu Glu Asp Leu Arg Gln Gly Leu Leu
                165                 170                 175

Pro Val Leu Glu Ser Phe Lys Val Ser Phe Leu Ser Ala Leu Glu Glu
                180                 185                 190

Tyr Thr Lys Lys Leu Asn Thr Gln
                195                 200
```

(2) INFORMATION FOR SEQ ID NO:16:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

ATCGATACCG CCATGAAAGC TGCGGTGCTG                       30

(2) INFORMATION FOR SEQ ID NO:17:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

ATGGGCGCGC GCGCAGTCGC GCATCTCCTC                       30

-continued (2) INFORMATION FOR SEQ ID NO:18:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

GAGGAGATGC GCGACTGCGC GCGCGCCCAT                                              30

(2) INFORMATION FOR SEQ ID NO:19:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

GTCGACGGCG CCTCACTGGG TGTTGAGCTT                                              30